United States Patent
Ford et al.

(10) Patent No.: US 9,527,808 B2
(45) Date of Patent: Dec. 27, 2016

(54) CONTINUOUS METHOD FOR PRODUCING ORTHO-SUBSTITUTED ANILINES IN A FLOW REACTOR

(71) Applicants: BAYER CROPSCIENCE AG, Monheim (DE); BAYER TECHNOLOGY SERVICES GMBH, Leverkusen (DE)

(72) Inventors: Mark James Ford, Schmitten (DE); Christian Severins, Leverkusen (DE)

(73) Assignees: Bayer CropScience AG, Monheim (DE); Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 14/427,471

(22) PCT Filed: Sep. 12, 2013

(86) PCT No.: PCT/EP2013/068878
§ 371 (c)(1),
(2) Date: Mar. 11, 2015

(87) PCT Pub. No.: WO2014/041052
PCT Pub. Date: Mar. 20, 2014

(65) Prior Publication Data
US 2015/0210637 A1    Jul. 30, 2015

(30) Foreign Application Priority Data
Sep. 17, 2012 (EP) .................. 12184687

(51) Int. Cl.
| C07C 211/00 | (2006.01) |
| C07C 319/20 | (2006.01) |
| C07D 251/16 | (2006.01) |
| C07D 209/34 | (2006.01) |
| C07D 251/20 | (2006.01) |
| C07D 403/04 | (2006.01) |

(52) U.S. Cl.
CPC ........... *C07C 319/20* (2013.01); *C07D 209/34* (2013.01); *C07D 251/16* (2013.01); *C07D 251/20* (2013.01); *C07D 403/04* (2013.01)

(58) Field of Classification Search
None
See application file for complete search history.

(56) References Cited

U.S. PATENT DOCUMENTS

| 3,972,894 A | 8/1976 | Gassma |
| 8,492,590 B2 | 7/2013 | Ford et al. |
| 2013/0281711 A1 | 10/2013 | Ford et al. |

FOREIGN PATENT DOCUMENTS

| WO | 9641799 A1 | 12/1996 |
| WO | 2010127786 A1 | 11/2010 |
| WO | 2012028162 A1 | 3/2012 |

OTHER PUBLICATIONS

Jiang et al., "Design, synthesis, and biological evaluations of novel oxindoles as HIV-1 non-nucleoside reverse transcriptase inhibitors. Part 2" Bioorganic and Medicinal Chemistry Letters. vol. 16: 2109-2112, (2006).
Clark et al., "Preparation of Indoles and Oxindoles from N-(tert-Butoxycarbonyl)-2-alkylanilines" Synthesis. pp. 871-878, (1991).
Johnson et al., "General Procedure for the Synthesis of o-Aminophenylacetates by a Modification of the Gassman Reaction" Journal of Organic Chemistry. vol. 55: 1374-1375, (1990).
Jones et al., "Intramolecular Reactions Using Amide Links: Aryl Radical Cyclisation of Silyated Acryloylanilides" Tetrahedron Letters. vol. 35, No. 41: 7673-7676, (1994).
Kikugawa et al., "Intramolecular Cyclization with Nitrenium Ions Generated from N-Chloro-N-methoxyamides in Neutral Conditions" The Chemical Society of Japan. pp. 1771-1774, (1987).

(Continued)

*Primary Examiner* — Jeffrey H Murray
(74) *Attorney, Agent, or Firm* — McBee Moore Woodward Vanik IP LLC

(57) ABSTRACT

Continuous process for preparing ortho-substituted anilines of the formula

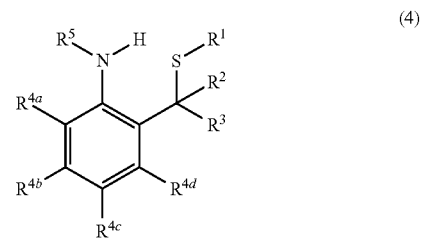

(4)

in a flow reactor in the presence of a nitrogen base not having an NH group, and multistage process for preparing herbicidal N-alkyl-N-[2-(1,3,5-triazin-2-ylcarbonyl)-phenyl]alkansulphonamides of the formula (4-1)

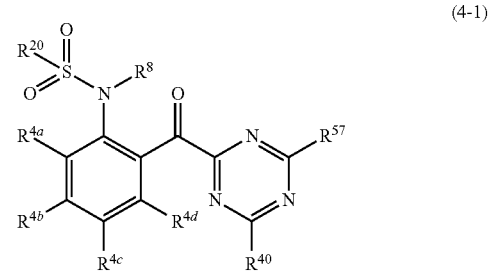

(4-1)

wherein the continuous process for preparing ortho-substituted anilines of the formula (4) in a flow reactor constitutes the first process step of the multistage process for preparing the herbicidal active ingredients of the formula (4-1).

12 Claims, No Drawings

(56) References Cited

OTHER PUBLICATIONS

Lengyel et al., "Synthetic Communications: An International Journal for Rapid Communication of Synthetic Organic Chemistry" Synthetic Communications. vol. 28, No. 10: 1891-1896, (1998).
Ward C. Sumpter, "The Chemistry of Oxindole" Chem. Rev.. vol. 37: 443-449, (1945).
Warpehoski et al., "Total Synthesis of U-71, 184, A Potent New Antitumor Agent Modeled on CC-1065" Tetrahedron Letters. vol. 27, No. 35: 4103-4106, (1986).
Hamada et al., "Photochemical Synthesis of 1,2,3,4-Tetrahydroisoquinolin-3-ones and Oxindoles from N-Chloroacetyl Derivatives of Benzylamines and Anilines" Chem. Pharm. Bull.. vol. 29, No. 1: 128-136, (1981).
Axon et al., "A New Radical Based Synthesis of Lactams and Indolones from Dithiocarbonates (Xanthates)" Tetrahedron Letters. vol. 35, No. 11 1719-1722, (1994).
Boivin et al., "A New Radical Based Synthesis of Lactams and Indolones from Dithiocarbonates (Xanthates)" Tetrahedron Letters. vol. 35, No. 51 9553-9556, (1994).
International Search Report from corresponding PCT/EP2013/068878, mailed Nov. 20, 2013.
Wright et al., "A Convenient Modification of the Gassman Oxindole Syntheis", Tetrahedron Letters, Elsevier, Amsterdam, NL, vol. 37, No. 27, Jul. 1, 1996, pp. 4631-4634, XP004028978.
Gassmann et al., "Oxindoles. A New, General Method of Synthesis", Journal of the American Chemical Society, Columbus, Ohio, Jan. 14, 1974, pp. 5508-5512.

CONTINUOUS METHOD FOR PRODUCING ORTHO-SUBSTITUTED ANILINES IN A FLOW REACTOR

CROSS REFERENCE TO RELATED APPLICATIONS

This application is a §371 National Stage Application of PCT/EP2013/068878, filed Sep. 12, 2013, which claims priority to EP 12184687.7, filed Sep. 17, 2012.

BACKGROUND

Field of the Invention

The invention relates to the field of chemical synthesis of biologically active compounds on the industrial scale, more particularly to the synthesis of ortho-substituted anilines as intermediates for the subsequent production of fine chemicals and of active ingredients for agriculture, using a flow reactor for continuous performance of the synthesis.

Description of Related Art

The selective exchange of hydrogen in an aromatic system for a substituted carbon atom is one of the fundamental reactions in organic chemistry and is thus known.

The class of compounds which can thus be prepared includes 2-oxindoles (dihydroindol-2-ones) and precursors thereof. Oxindoles and precursors thereof are versatile intermediates for active ingredient syntheses (Bioorg. Med. Chem. Lett. 2006, 16, 2109; JP 2008-101014; WO 96/41799 A1).

Most of the described syntheses of oxindoles, called Stolle syntheses (see scheme 1 (a)), use a variation of the Friedel-Crafts reaction (Stolle Synthesis, W. C. Sumpter, Chem. Rev. 1945, 37, 443-449). However, Stolle syntheses are only of limited utility, since the performance thereof requires strongly acidic conditions and the use of an electron-rich aniline.

Additionally known are free-radical reactions (see scheme 1 (b)), nitrenium ion reactions and organolithium reactions, and also photochemical methods. However, the usability thereof is likewise limited by the type of oxindoles to be prepared in each case, the compatibility of substrates, the reaction conditions, and the condition that the aromatic must already have a substitutable halogen substituent.

Free-radical processes (see scheme 1(b)) are described in: Zard et al., Tetrahedron Lett. 1994, 35, 9553-9556; Zard et al., Tetrahedron Lett. 1994, 35, 1719-1722; Jones et al., Tetrahedron Lett. 1994, 35, 7673-7676; Kikugawa et al., Chem. Letters 1987, 1771-1774; Clark et al., Synthesis 1991, 871-878; Yonemitsu et. al., Chem. Pharm. Bull. 1981, 29, 128-136.

Scheme 1-known oxindole syntheses:

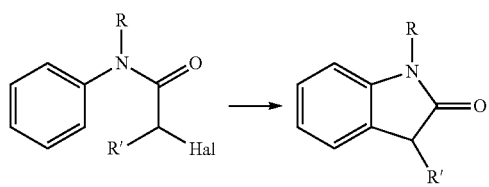

(a)

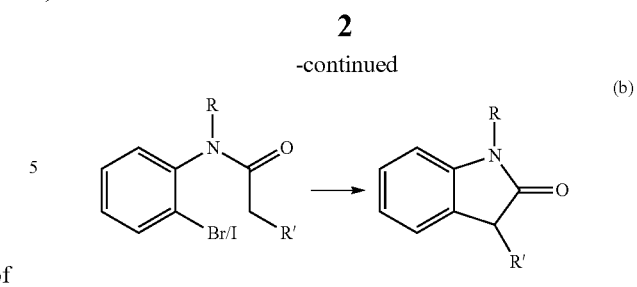

(b)

The process of Gassman et al. (Organic Synthesis Coll., Vol. 6, 601 and Vol. 56, 72), which proceeds from aniline and methyl thioacetate ester, via chlorination and treatment with triethylamine at −70° C. (see scheme 2), appears to be suitable with regard to performability, availability of reactants, duration of reaction (reaction rate) and reproducibility.

However, it is known that good yields can be achieved only at low temperatures, namely when the unstable N-chloro (1) or N-sulphonium (2) intermediates which occur during the reaction (see scheme 2) are formed below −65° C., normally at −78° C. (Gassman et. al., J. Am. Chem. Soc., 1974, 96(17), 5508; Gassman et al., J. Am. Chem. Soc., 1974, 96(17), 5512; WO 96/41799 A1). However, the performance of a reaction on the industrial scale at temperatures below −65° C. already entails higher apparatus complexity and is additionally disadvantageous owing to the high operating costs caused by the cooling.

Scheme 2 - Reaction profile according to Gassman via aniline chlorination:

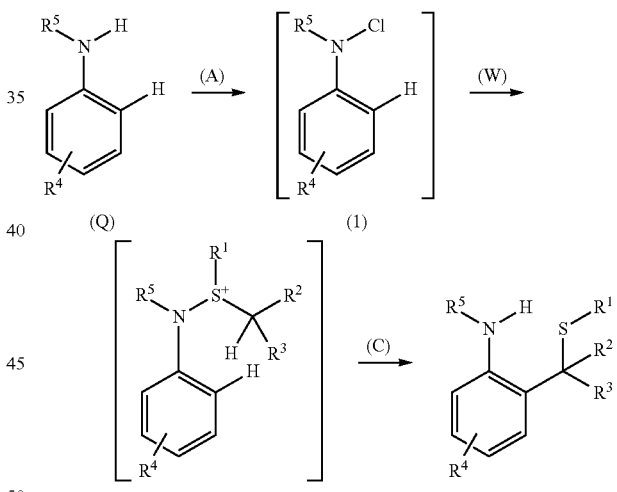

Q = aniline
A = chlorinating agent (e.g.: tert-butyl hypochlorite, t-BuOCl)
W = thioether ($R^1$—S—$CHR^2R^3$)
C = tertiary amine base (e.g.: triethylamine)

The chlorinating agent of choice, according to the literature, is the unstable and explosive tert-butyl hypochlorite, in which case the by-product of the chlorination gives the neutral tert-butyl alcohol. In the few cases in which sulphuryl chloride ($SO_2Cl_2$) has been used as a chlorinating agent, a second, non-nucleophilic base such as "proton sponge" was used (Johnson, J. Org. Chem. 1990, 55, 1374; Warpehoski, Tetrahedron Lett. 1986, 27, 4103). Since both variants have to be performed at low temperatures, however, this is not an advantageous solution for performance of the reaction on the industrial scale. In the Gassman process, the tertiary amine base (C) is not added until the final step (see scheme 2) and serves to deprotonate the intermediate (2) to initiate the conversion of the intermediate (2) to the ortho-substituted aniline (4).

WO 2012/028162 A1 discloses an improved batch process for preparing compounds of the formula (4), likewise proceeding from a thioether and an aniline of the formula (Q), wherein the chlorinating agent used is likewise sulphonyl chloride ($SO_2Cl_2$).

The core of the teaching disclosed in WO2012/028162 A1 relates to the finding that an excess of the surprisingly electron-poor anilines functions as a mild base in the formation of product of the formula (4). This is surprising with respect to the standard Gassman reaction, which teaches the final addition of an additional tertiary amine (cf. schemes 2 and 3: C=tertiary amine base, e.g.: triethylamine). The aniline is obviously capable of catalysing the rearrangement to the product of the formula (4) and therefore also of eliminating HCl from a chlorosulphonium intermediate of the formula (3), which would lead only to side reactions. There are no pointers in the document cited to particular measures for performance of the reaction disclosed in WO 2012/028162 A1 using a flow reactor for continuous performance of the synthesis.

For the synthesis of oxindoles, the product (4) obtained by the use of the Gassman reaction is a key precursor. A new alternative for further conversion of compounds (4) to the respective oxindole is described in WO 2010/127786 A1.

A further alternative for preparation of ortho-substituted anilines of the formula (4) is described by Wright et al. (Tetrahedron Lett. 1996, 37, 4631). This involves preparing the chlorosulphonium intermediate (3) from a sulphoxide and oxalyl chloride and further conversion to the product of the formula (4) (see scheme 3). In the process described by Wright et al., the tertiary amine base (C) is not added until the final step (see scheme 3).

However, the chlorosulphonium intermediate (3) is likewise unstable. Moreover, for this reaction, the sulphoxide first has to be prepared and isolated. For reasons of stability, the reaction likewise has to proceed at low temperatures, namely at –78° C. In addition, the reaction has to be conducted stepwise in order to avoid a reaction between aniline and oxalyl chloride.

Scheme 3 - Reaction profile via chlorosulphonium intermediate:

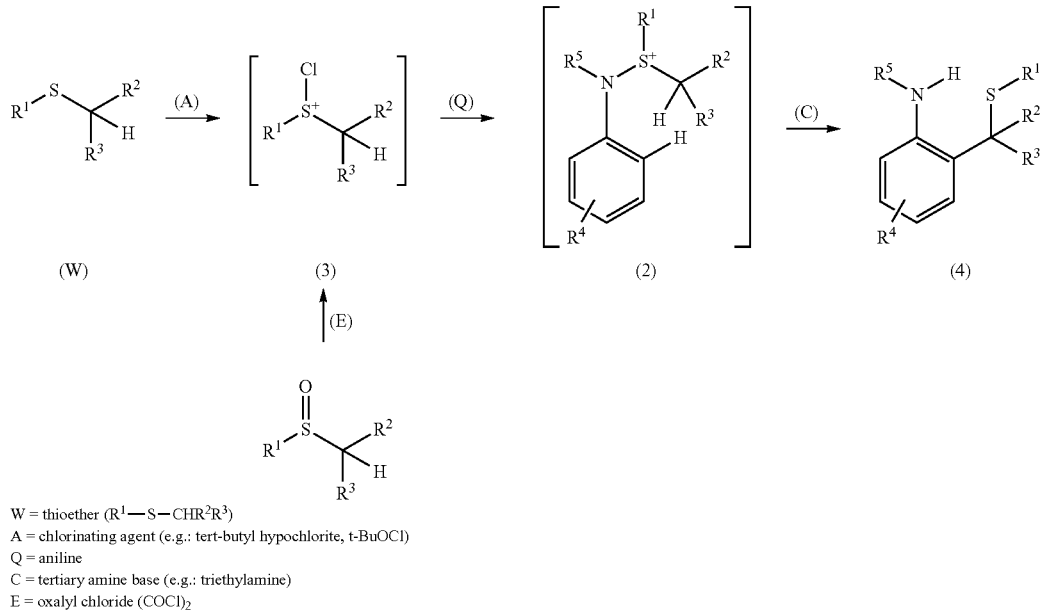

W = thioether ($R^1$—S—$CHR^2R^3$)
A = chlorinating agent (e.g.: tert-butyl hypochlorite, t-BuOCl)
Q = aniline
C = tertiary amine base (e.g.: triethylamine)
E = oxalyl chloride ($COCl)_2$ U.S. Pat. No. 3,972,894 discloses a further batch process developed by Gassman, in which oxindoles are prepared by first preparing ortho-substituted anilines as intermediates. The reactants used to obtain the ortho-substituted anilines are N-haloanilines and β-thioesters or β-thioamides. The conversion of the reactants likewise forms an azasulphonium compound of the formula (2) as an intermediate, and this is likewise only reacted with a base to give an ortho-substituted aniline in the final step (see scheme 2). Suitable bases mentioned are relatively short-chain alkylamines, such as ethylamine, diethylamine, triethylamine, tributylamine, and aromatic amines, for example pyridine. There are no pointers in the document cited to particular measures for performance of the reaction disclosed in U.S. Pat. No. 3,972,894 using a flow reactor for continuous performance of the synthesis.

The reasons for the sensitivity of the reactions shown in scheme 3 to relatively high reaction temperatures, i.e. to reaction temperature exceeding –70° C., and the reasons for the necessity of always performing the reaction stepwise, are various.

It is firstly essential that the functional groups in the reaction shown in scheme 3, i.e. the nitrogen atom of the aniline and the sulphur atom of the thioether, occur unchanged both in the product (4) and in the reactant.

Against this background, a selective chlorination in which the product (4) is formed directly, i.e. during the reaction, and simultaneously with high yield, i.e. quantitatively, would not be expected. This also explains why all methods known from the literature use, or suggest, a stepwise reaction regime.

Moreover, in the chlorination of compounds such as anilines, the problem of ring chlorination arises, i.e. that of unwanted chlorination of the aromatic benzene ring rather than the desired chlorination of the amino substituent. As a result of ring chlorination, the N-chloroaniline can be converted to a ring-chlorinated aromatic at reaction temperatures exceeding −65° C. (see scheme 4).

According to Lengyel et al., the problem of ring chlorination can be illustrated by the example of acetanilide. The probability of ring chlorination depends on whether the benzene ring is electron-rich or rather electron-poor. Even though acetanilide is much less electron-rich compared to N-chloroaniline and should thus have a much lower tendency to ring chlorination, ring chlorination proceeds with tert-butyl hypochlorite as the chlorinating agent even at a reaction temperature of 0° C. (Lengyel et al. Synth. Comm., 1998, 28 (10), 1891-1896).

Furthermore, the sulphonium intermediates (2) or (3) in the presence of bases can form the reactive by-product (5) through elimination. The reactive by-product (5) can condense, for example, with an aniline. In this case, the Pummerer oxidation of the $R^2$—CH—$R^3$ radical irreversibly produced the secondary component (6) (see scheme 4). In addition, other oxidation products (dimers) can also form.

Scheme 4 - Possible side reactions in the preparation of a compound of the formula (4):

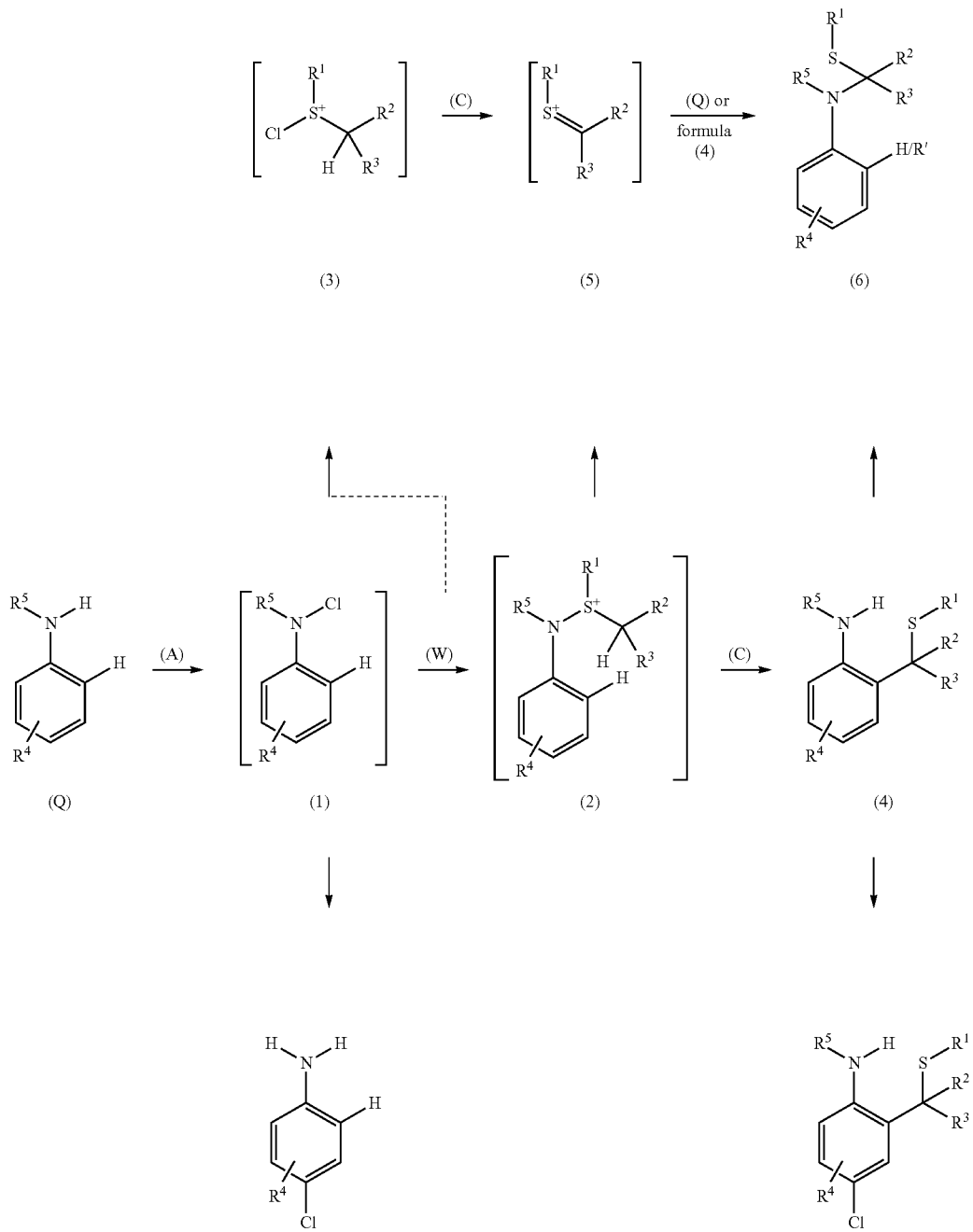

(The designations of the reactants and the other reagents in scheme 4 correspond to the designations from scheme 3.)

WO 2010/127786 A1 describes how some of the aforementioned disadvantages can be overcome, and the executability of an industrial batch reaction is demonstrated by examples. In the case of performance of a batch reaction according to WO 2010/127786 A1, however, temperatures below −20° C. are regarded as necessary, and so the performance of the batch reaction on the industrial scale gives rise to high energy costs. Moreover, the repeated requirement for cooling of the batch vessel proceeding from room temperature to below −20° C. takes a lot of time.

Against this background, it would be a considerable advantage if it were possible to perform the reaction for preparation of compounds of the formula (4) in a flow reactor.

In a flow reactor, a small volume compared to the batch reaction has to be brought to low temperature, and the further reaction can be performed continuously, i.e. without interruption. The advantages of use of a flow reactor consist, in general terms, in the improvement of productivity with a simplified process procedure.

However, the application of the reaction conditions envisaged for the performance of a batch reaction and disclosed in WO 2010/127786 A1 to the conditions in a flow reactor, i.e. the application of the conditions to the continuous performance of the reaction in a flow reactor, was found to be problematic and impracticable due to the formation of sparingly soluble salts in the reaction mixture alone.

In fact, reactions in which salts are formed are very difficult to accomplish in flow reactors if these salts precipitate as solids. Such solids in a flow reactor cause the incrustation and blockage of the microchannels and small-volume mixing chambers. However, the function of a flow reactor system is based specifically on the accessibility of these microchannels and mixing chambers. The precipitates formed during the reaction and the suspensions which arise therefrom should therefore absolutely be avoided if a reaction is to be performable in a flow reactor without interruption and in a reliable manner. Also particularly unfavourable is the occurrence of sparingly soluble salts and/or of viscous suspensions if a reaction is to be executed with a concentration of industrial relevance, i.e. on the industrial scale.

The use of the conditions disclosed in WO 2010/127786 A1, which are directed solely to the performance of the batch process, in the continuous performance of the reaction in a flow reactor was found to be very problematic.

The difficulties could be based on the fact that the aniline used as the reactant in the present process is chlorinated in the presence of a chlorinating agent during the reaction because of its basic properties. The chlorination gives rise to HCl, but at least some of the chlorinated aniline precipitates out as the solid HCl salt in the presence thereof.

In a batch reaction, these precipitates, in contrast to the performance of the same reaction in a flow reactor, are not troublesome to any greater degree, because the HCl salt of the aniline is in equilibrium with the free aniline. This is true even when the equilibrium is established only slowly owing to the solubility of the salt. In a batch reaction, this equilibrium can be re-established again and again with progressive chlorination, and so new aniline is repeatedly available for the reaction in spite of the decreasing amount of free aniline.

In the case of performance of the same reaction in a flow reactor, in contrast, the boundary conditions for the new establishment of the equilibrium do not exist. The main reason for this is the comparatively short residence time of the reactants in the respective reactor section provided for the running of the reaction in the flow reactor. Therefore, the establishment of a chemical equilibrium can proceed only to a very limited degree, if at all, in the respective section of a flow reactor.

In the case of application of the conditions established for the batch reaction to the performance of the same reaction in a flow reactor, the reactant precipitates out as the aniline-HCl salt. This salt formation gives rise to a thick, i.e. highly viscous, suspension. This suspension cannot be conveyed, and so the passage of the reaction mixture through the components which form the flow reactor is either made very difficult or is impossible.

Moreover, the salt formation removes the aniline reactant from the reaction, and so an excess of chlorinating agent arises in the next reaction section of the flow reactor. This excess increases the probability that unwanted side reactions will occur, more particularly the unwanted chlorination of the thioether likewise used as the reactant.

SUMMARY

Against this background, it is an object of the invention to provide a modified process which enables the preparation of ortho-substituted anilines of the formula (4) proceeding from anilines of the formula (Q) on the industrial scale using a flow reactor. More particularly, it is an object of the invention to provide a continuous process for preparing ortho-substituted anilines of the formula (4) with avoidance of viscous solids-containing suspensions during the performance of the reaction in a flow reactor.

In the course of the initial efforts to achieve the object, it was found that, surprisingly the addition of at least one nitrogen base not having an NH group as early as the start of the reaction improved the solubility of the reaction mixture overall.

The invention thus provides a process for continuously preparing compounds of the formula (4)

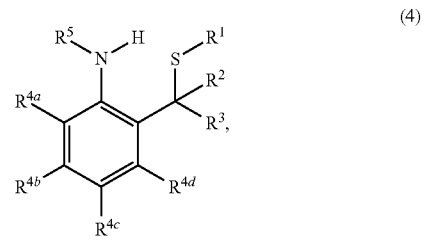

(4)

in which
$R^1$ is $(C_1\text{-}C_6)$ alkyl, substituted $(C_1\text{-}C_6)$ alkyl, aryl or substituted aryl,
$R^2$ is an electron-withdrawing or activating substituent selected from the group consisting of
CN,
$NO_2$,
CO—$R^{1'}$, where $R^{1'}$ is as defined for $R^1$ and $R^{1'}$ is the same as or different from $R^1$,
CO—X, where X is $OR^{1''}$, $SR^{1''}$ or $NR^{2'}R^{2''}$, in which $R^{1''}$ is as defined for $R^1$ and $R^{1''}$ is the same as or different from $R^1$, and in which
$R^{2'}$ and $R^{2''}$ are each independently H, $(C_1\text{-}C_6)$ alkyl, substituted $(C_1\text{-}C_6)$ alkyl, aryl or substituted aryl, or $R^{2'}$ and $R^{2''}$ alternatively form a ring, SO(n)-$R^{1'''}$, where $R^{1'''}$ is as defined for $R^1$, where each $R^{1'''}$ is the same as or different from $R^1$ and where n is 0, 1 or 2, aryl, and heteroaryl, $R^3$ is H, ($C_1$-$C_6$) alkyl, substituted ($C_1$-$C_6$) alkyl, aryl or substituted aryl, $R^{4a}$ to $R^{4d}$ are each independently selected from the group consisting of hydrogen, fluorine, chlorine, bromine, iodine, CN, $NO_2$, and from ($C_1$-$C_6$)-alkyl, where the alkyl radical is unsubstituted or substituted by one or more substituents selected from the group consisting of fluorine, chlorine, ($C_1$-$C_4$)-alkoxy and ($C_3$-$C_7$)-cycloalkyl, ($C_3$-$C_7$)-cycloalkyl, where the cycloalkyl radical is unsubstituted or substituted by one or more substituents selected from the group consisting of fluorine, chlorine, ($C_1$-$C_4$)-alkyl and ($C_3$-$C_7$)-cycloalkyl and ($C_1$-$C_4$)-alkoxy, ($C_1$-$C_6$)-alkoxy, where the alkoxy radical is unsubstituted or substituted by one or more substituents selected from the group consisting of fluorine, chlorine, ($C_1$-$C_4$)-alkoxy and ($C_3$-$C_7$)-cycloalkyl, ($C_3$-$C_7$)-cycloalkoxy, where the cycloalkoxy radical is unsubstituted or substituted by one or more substituents selected from the group consisting of fluorine, chlorine, ($C_1$-$C_4$)-alkyl and ($C_1$-$C_4$)-alkoxy, CO—X, where X is $OR^{1'''}$, $SR^{1'''}$ or $NR^{2'}R^{2''}$, in which $R^{1'''}$ is as defined for $R^1$ and $R^{1'''}$ is the same as or different from $R^1$, and in which $R^{2'}$ and $R^{2''}$ are as defined for $R^3$, where $R^{2'}$ and $R^{2''}$ are each the same as or different from $R^3$, or $R^{2'}$ and $R^{2''}$ form a ring, phenyl or 1-naphthyl or 2-naphthyl or a five- or six-membered heteroaromatic ring having 1 to 2 heteroatoms, where the heteroatoms are each independently selected from the group consisting of O and N, and where the aryl or heteroaryl radical is unsubstituted or substituted by one or more substituents selected from the group consisting of fluorine, chlorine, bromine, iodine, ($C_1$-$C_4$)-alkyl, ($C_1$-$C_4$)-alkoxy and ($C_3$-$C_7$)-cycloalkyl and ($C_1$-$C_4$)-alkylthio, and $R^5$ is H, ($C_1$-$C_6$) alkyl, substituted ($C_1$-$C_6$) alkyl, aryl or substituted aryl, in which the reactants used in a flow reactor in the presence of an organic solvent are an aniline (Q)

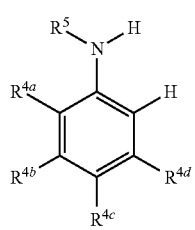

(Q)

in which $R^{4a}$ to $R^{4d}$ and $R^5$ are each as defined for compounds of the formula (4), and a thioether (W)

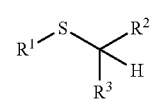

(W)

in which $R^1$, $R^2$ and $R^3$ are each as defined for compounds of the formula (4), wherein the reactants of the formulae (Q) and (W) are converted in the presence of a chlorinating agent, and at least one nitrogen base having no NH group.

DETAILED DESCRIPTION OF A PREFERRED EMBODIMENT

Preference is given to compounds of the formula (4) in which the $R^{4a}$ to $R^{4d}$ radicals are each independently H, F, Cl, Br, I, $CF_3$, CN, $NO_2$ or CO—X, where X is $OR^{1'''}$, $SR^{1'''}$ or $NR^{2'}R^{2''}$, in which $R^{1'''}$ is as defined for $R^1$ and $R^{1'''}$ is the same as or different from $R^1$, and in which $R^{2'}$ and $R^{2''}$ are each independently H, ($C_1$-$C_6$) alkyl, substituted ($C_1$-$C_6$) alkyl, aryl or substituted aryl. The $R^{2'}$ and $R^{2''}$ radicals may alternatively also form a ring.

Proceeding from compounds of the formula (4), oxindole compounds of the formula (7-1)

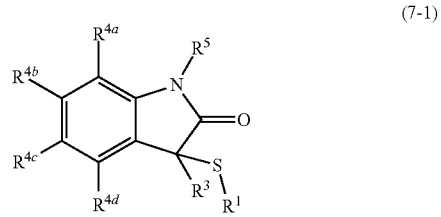

(7-1)

are obtained by the extraction of the tertiary amine from the reaction solution containing the compounds of the formula (4), or by the concentration of the reaction solution containing the compounds of the formula (4) and subsequent admixing of the concentrate with an alcoholic HCl solution, preferably 0.4 N HCl, with further stirring at a temperature in the range from 0° to 40° C.

It is a feature of the process according to the invention that a nitrogen base not having an NH group is added to the reaction mixture from the start. The addition of the nitrogen base prevents the precipitation of already chlorinated aniline molecules as the HCl salt.

It is a feature of the nitrogen base already added at the start of the reaction, and optionally added repeatedly in the course of the reaction, that it does not have any hydrogen bonded to the nitrogen, i.e. has no NH group. Nitrogen bases not having an NH group can also be referred to as "amines without free NH". A large group of nitrogen bases not having an NH group is that of tertiary amines. The amines usable for the performance of the process according to the invention are also notable for their basic properties.

As well as tertiary amines, unsubstituted pyridines or substituted or unsubstituted quinolines are also nitrogen bases, each of which likewise do not have an NH group and are suitable for performance of the process according to the invention.

The core of the invention relates to the unexpected and simultaneously very advantageous fact that the HCl salt of a nitrogen base without an NH group formed in the presence of a chlorinating agent, especially the HCl salt of one of the preferred nitrogen bases mentioned in the previous paragraph, formed in the presence of a chlorinating agent, is present dissolved in the solvent selected for preparation of compounds of the formula (4) over the entire reaction.

The advantage is based on the fact that the nitrogen bases take up the HCl which forms in the presence of the chlorinating agent without being chlorinated themselves, while remaining dissolved in the solvent selected for the performance of the reaction for preparation of compounds of the formula (4). Thus, the addition of one of the nitrogen bases mentioned achieves the effect that the aniline reactant does not precipitate out as the insoluble HCl salt.

The use of nitrogen bases of which none has an NH group also results in the avoidance of other side reactions. For instance, in the presence of a chlorinating agent, in the case of an amine base with "free H", for example in the case of a secondary amine, an N—Cl bond can form. The chlorinated amine can react in an unwanted side reaction with the thioether (W), such that the thioether is removed as a reactant from the desired main reaction.

In addition, the structure of the flow reactor, which is usable after avoidance of sparingly soluble or viscous reaction mixtures, results in a rapid spatial separation of reactants and products. Through the rapid spatial separation of the reactants from the products in a flow reactor, the new chlorination of the already chlorinated reaction product of the formula (4) can additionally be avoided.

Regardless of the problem of formation of aniline-HCl salts which precipitate out in solid form during a chemical reaction, it should first be considered with regard to the present process that, according to the state of knowledge to date, no consideration would be given to the addition of a tertiary amine to the reaction mixture before conclusion of the chlorination in a reaction according to scheme 2 for avoidance of side reactions (see scheme 4).

Furthermore, with regard to the delimitation of the present invention from the known (original) Gassman process (see scheme 2), it is found that the formation of the compound (2) is already complete in the original Gassman process before a tertiary amine is added to the reaction mixture. In the original Gassman process, the tertiary amine is added alone in order to catalyse the conversion of compounds of the formula (2) to the compounds of the formula (4) by means of deprotonation.

It would have been expected that the addition of a tertiary amine as early as the start of the reaction, in a reaction according to scheme 2, would lead to unwanted chlorination of the tertiary amine. The chlorine salt of the tertiary amine formed by the chlorination is a non-inert, i.e. reactive, species. It would have been expected that this reactive species would result in unwanted side reactions, for example the chlorination or amination of the thioether used as the reactant. Probably for these reasons, in the case of a reaction according to scheme 2, the addition of a nitrogen base without an NH group as early as the start of the reaction has not been known to date.

The present process for continuously preparing an ortho-substituted aniline of the formula (4) in a flow reactor in the presence of a nitrogen base not having an NH group is associated with the significant advantage that the HCl salt of the nitrogen base used is present dissolved in the organic solvent selected for the reaction throughout the reaction, i.e. at the different temperatures which exist in the respective components of the flow reactor.

An essential aspect relating to the invention is thus, as well as the selection of a suitable nitrogen base, attention to and prior assessment of the solubility of the HCl salt of the nitrogen base, i.e. the assessment of the solubility of the salt which forms from the nitrogen base selected in each case in the presence of the chlorinating agent used in the reaction.

Solubility and miscibility of the reactants are essential prerequisites for the conversion of the reactants in a flow reactor, in that the latter is based on a continuous reaction regime. Because of the solubility of the HCl salt of the nitrogen base, it is possible to mix the aniline (Q), the chlorinating agent and the thioether (W) rapidly together and/or successively, and convert them directly to compounds of the formula (4).

The selective running of the reaction, which additionally also gives rise to the product in high purity, is particularly surprising because the nitrogen base competes with the aniline for the chlorine atom in the course of chlorination. In an unwanted side reaction, the chlorinated nitrogen base can react with thioether. In this unfavourable, but likewise probable, case, the thioether would no longer be available as a co-reactant for the aniline. In this context, it is not possible, even for a person skilled in the art, to predict whether, or to what extent, the addition of the tertiary amine (P) will adversely affect the selectivity of the reaction between the reactants, i.e. between the aniline (Q) and the thioether (W), after preceding addition of a chlorinating agent.

The reaction temperature in the course of performance of the reaction in the flow reactor is preferably between $-65°$ C. and $0°$ C. It is particularly preferable when the reaction temperature is between $-55°$ C. and $-10°$ C. Most preferable is a reaction temperature between $-45°$ C. and $-20°$ C.

A preferred group of nitrogen bases without an NH group (P) is the group of the tertiary amines. Particularly preferred tertiary amines are trialkylamines whose alkyl radicals have a chain length of $C_1$-$C_{18}$.

The alkyl groups of these tertiary amines may also be joined to form a ring, so as to give cyclic tertiary amines. A preferred cyclic tertiary amine is piperidine. With regard to the process according to the invention, a substituted pyridine is equivalent to a tertiary amine, since a pyridine enters into identical, or at least similar, reactions which are also typically entered into by a tertiary amine. For instance, it is also possible to use benzofused ring systems of pyridine.

In the case of pyridines, it is preferable when they are substituted at least by one alkyl, alkoxy or halogen radical to ensure that they are soluble. Particularly preferred substituents of the pyridine are alkyl radicals and alkoxy radicals having a chain length of $C_1$-$C_{18}$.

As well as pyridine, other heteroaromatics are also suitable in principle for performance of the process according to the invention. In this case, the basicity of these heteroaromatics must be equal to or higher than the basicity of the aniline (Q).

These nitrogen bases without an NH group can be used alternatively or in combination with one another. A mixture may, as well as a tertiary amine, comprise a substituted pyridine and/or a benzofused ring system of pyridine. Alternatively, the base mixture may comprise a substituted pyridine and/or a benzofused ring system of pyridine.

The pyridine substituents are preferably selected from the group consisting of alkyl, alkoxy and halogen radicals, particular preference being given to a chain length of $C_1$-$C_{18}$ in the case of alkyl radicals and alkoxy radicals.

Particularly preferred tertiary amines are trialkylamines wherein the alkyl radicals have a chain length of $C_1$-$C_{18}$, at least one of the radicals having a chain length of at least $C_4$-$C_{18}$. This minimum chain length of six carbon atoms in at least one of the three radicals of the trialkylamine ensures that the tertiary amine is sufficiently lipophilic to ensure the solubility of the tertiary amine in the organic solvent selected. If the two remaining radicals among the radicals of the trialkylamine likewise have a minimum chain length of six carbon atoms, the lipophilicity of the amine is correspondingly higher. In this context, appropriate combinations of the chain lengths of all alkyl radicals to give a total chain length of at least $C_4$-$C_{18}$ may also be sufficient to ensure the solubility of the HCl salt. The alkyl radicals of the trialkylamine in this case may each be unsubstituted or substituted.

A trialkylamine which is very particularly preferred for the present process is tributylamine.

A very particularly preferred pyridine is 2-methyl-5-ethylpyridine.

A very particularly preferred benzofused ring system of pyridine is substituted or unsubstituted quinoline, unsubstituted quinoline being the most preferred.

It is also conceivable that the process is performed in a mixture of nitrogen bases, in which case the mixture consists of
  a tributylamine and 2-methyl-5-ethylpyridine,
  a tributylamine and an unsubstituted quinoline, or of
  a mixture of 2-methyl-5-ethylpyridine and an unsubstituted quinoline.

Alternatively, a mixture consisting of three of these nitrogen bases is also usable. The most preferred base mixture comprising three nitrogen bases comprises tributylamine, an unsubstituted quinoline and 2-methyl-5-ethylpyridine.

The process according to the invention can be performed with various solvents, provided that the HCl salt of the nitrogen base is dissolved in this solvent at the reaction temperature selected.

The fulfillment of the aforementioned prerequisite is essential for the performance of the process. In addition, the solvent must be compatible with the chlorinating agent.

These demands are met by nonpolar organic solvents, such as
  chloroalkanes (for example dichloromethane and dichloroethane),
  aromatics (for example benzene, toluene, xylene),
  haloaromatics (for example chlorobenzene, dichlorobenzene),
  substituted aromatics (for example benzotrifluoride, chlorobenzotrifluoride, chlorotoluene, chloroxylene) alone, or
  a mixture comprising one or more of the aforementioned nonpolar inorganic solvents.

As well as nonpolar organic solvents, as described in WO 2010/127786 A1, suitable solvents for performance of the inventive reaction are also polar organic solvents, preferably ester solvents, for example ($C_1$-$C_6$) alkyl acetate (for example methyl acetate, ethyl acetate, n-propyl acetate, isopropyl acetate, 2-methylprop-1-yl acetate, n-butyl acetate, but-2-yl acetate, pentyl acetates, hexyl acetates and cycloalkyl acetates, ($C_1$-$C_6$) alkyl and cycloalkyl propionates, ($C_1$-$C_6$) alkyl and cycloalkyl n-butyrates, isobutyrates, pentanoates and hexanoates and cyclopentanoates and cyclohexanoates), or a mixture comprising one or more of the aforementioned nonpolar organic solvents.

Useful chlorinating agents include all the chlorinating agents which are soluble in the organic solvent and are known to the person skilled in the art for this purpose.

Preferred chlorinating agents are tert-butyl hypochlorite and sulphuryl chloride, both of which are advantageously liquid and also have good solubility in one of the solvents mentioned. The two chlorinating agents mentioned can also be used together, i.e. in a mixture with one another. The chlorinating agent is more preferably sulphuryl chloride ($SO_2Cl_2$).

In a preferred embodiment of the invention, it is envisaged that, in a first mixing chamber, prior to the combination of the two reactants and prior to addition of the chlorinating agent, at least one of the two reactants
  is dissolved in an organic solvent, and
  mixed with at least one nitrogen base which does not have an NH group and is present dissolved in the organic solvent selected at the respective reaction temperature.

An essential aspect of the process according to the invention relates to the performance as a continuous reaction in a flow reactor. The possibility of multiple addition, i.e. of repeated addition, of a nitrogen base without an NH group, or of a mixture thereof, in various reaction stages is an essential parameter in the process regime. In the case of performance of the continuous reaction in a flow reactor, the reaction stages are defined by the various reservoir chambers, mixing chambers and delay zones which form part of the flow reactor and are arranged successively according to the reaction sequence.

In principle, the base is already added to the reactants in the reservoir chamber(s).

In a preferred embodiment, the nitrogen base can also be added again to the reaction mixture after combination of the two reactants dissolved in an organic solvent and after addition of the chlorinating agent, but prior to charging of the dwell zone which forms part of the flow reactor with the reaction mixture.

The repeated addition of the nitrogen base ensures that the viscosity of the reaction mixture meets the operational requirements in the respective section of the flow reactor, i.e. in the reservoir chambers, the mixing chambers and the dwell zones.

The solubility of the reaction mixture in the dwell zones of a flow reactor is particularly important for the usability of the flow reactor. This is especially true for ensuring that the operating requirements of the first dwell zone which forms part of a flow reactor are met.

Accordingly, it is within the scope of the process according to the invention that a nitrogen base which does not have an NH group and whose HCl salt is present dissolved in the organic solvent selected at the respective reaction temperature is added again to the reaction mixture after it has passed through the first dwell zone which forms part of the flow reactor and before the second dwell zone which forms part of the flow reactor is charged with the reaction mixture.

The effect of the new addition is that the viscosity of the reaction mixture meets the operational requirements of a flow reactor, especially the operational requirements of a second dwell zone which forms part of a flow reactor.

It is within the scope of the invention that a nitrogen base which does not have an NH group and whose HCl salt is present dissolved in the organic solvent selected at the respective reaction temperature is added again to the respective reaction mixture each time after it leaves a dwell zone, i.e. before the charging of the downstream dwell zone.

The performance of the new, i.e. repeated, addition of the nitrogen base is demonstrated by synthesis Example 1, and corresponds to the very particularly preferred embodiment of the process according to the invention elucidated hereinafter.

In a very particularly preferred embodiment of the process, it is envisaged that a first reservoir chamber (RC1) of the flow reactor is initially charged with a reservoir mixture 1 (RM1) at least comprising an aniline (Q):

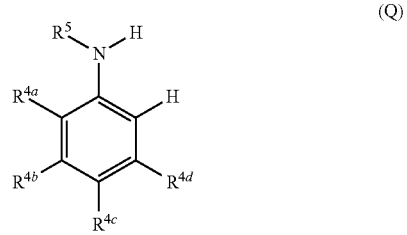

in which the $R^{4a}$ to $R^{4d}$ and $R^5$ radicals are each as defined in formula (4),
an organic solvent in which the aniline (Q) is dissolved, and
at least one nitrogen base not having an NH group, and
a second reservoir chamber (RC2) of the flow reactor is initially charged with a reservoir mixture 2 (RM2) at least comprising
a liquid chlorinating agent and
an organic solvent corresponding to the solvent present in the first reservoir chamber,
and
then reservoir mixture 1 (RM1) and reservoir mixture 2 (RM2) are mixed in a first mixing chamber (M1) at a reaction temperature in the range between −65° C. and 0° C., and
then the reaction mixture from the first mixing chamber (M1) is combined in a second mixing chamber (M2) with a reservoir mixture 3 (RM3) initially charged in a third reservoir chamber (RC3) of a flow reactor, at least comprising
a thioether (W)

in which the $R^1$, $R^2$ and $R^3$ radicals are each as defined in formula (4),
an organic solvent corresponding to the solvent initially charged in the first reservoir chamber, and
a nitrogen base which does not have an NH group and corresponds to the nitrogen base initially charged in the first reservoir chamber,
and the mixture thus obtained
is then converted in a first dwell element 1 (DE-1) of the flow reactor, and
then the mixture converted in the dwell element 1 (DE-1) is mixed again in a third mixing chamber (M3) of the flow reactor with a nitrogen base which does not have an NH group and corresponds to the nitrogen base initially charged in the first reservoir chamber, and the mixture thus obtained
is then converted again in a second dwell element 2 (DE-2) of the flow reactor to give a compound of the formula (4).

The aforementioned mixtures of an aniline (Q) and a nitrogen base without an NH group, or of a thioether (W) and a nitrogen base without an NH group, are preferably diluted beforehand with a solvent or a solvent mixture, in which case the mixture can be cooled in advance by precooling the feed lines to the mixing chambers (M).

It is likewise possible to predilute solely the nitrogen base (amount Z") with a solvent or alternatively with a solvent mixture, and additionally to precool it by precooling the feed lines to mixing chambers (M).

The chlorinating agent can also be prediluted with a solvent or a solvent mixture and can preferably be precooled by precooling the feed lines to the mixing chambers.

The amounts of the two reactants used, i.e. of the aniline of the formula (Q) and of the thioether of the formula (W), and the amounts of the chlorinating agents and of the nitrogen base used, are each variable over a wide range.

Preference is given to the following use amounts: up to 1 equivalent, preferably 0.5 to 1.0 equivalent, more preferably 0.7 to 1.0 equivalent and especially preferably 0.8 to 0.95 equivalent of the chlorinating agent are mixed with a mixture containing 1 equivalent of the aniline (Q) and up to 1 equivalent, preferably 0.1 to 0.9 equivalent, more preferably 0.2 to 0.5 equivalent and especially preferably 0.25 to 0.35 equivalent of the nitrogen base (amount Z) in a mixing chamber of a flow reactor.

The mixture thus obtained is mixed directly with a mixture of one equivalent of the thioether (W) and up to 1 equivalent, preferably 0.1 to 0.9 equivalent, more preferably 0.5 to 0.8 equivalent and especially preferably 0.65 to 0.75, equivalent of the nitrogen base (amount Z'), in each case in the mixing chamber of a flow reactor, the total amount of amine (Z+Z') being greater than or equal to the equivalent of the chlorinating agent. After passing through a dwell zone, the mixture is mixed with up to 2 equivalents, preferably 0.5 to 1.8 equivalents and more preferably 1.0 to 1.6 equivalents of the nitrogen base (amount Z").

The reactants used in connection with the present invention and the chemical terms used in this description will be elucidated in detail hereinafter.

The aniline (Q) used in the process according to the invention has the following structure:

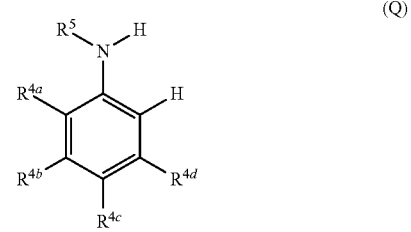

in which
$R^{4a}$ to $R^{4d}$ are each independently selected from the group consisting of hydrogen, fluorine, chlorine, bromine, iodine, CN, $NO_2$, and from
($C_1$-$C_6$)-alkyl, where the alkyl radical is unsubstituted or substituted by one or more substituents selected from the group consisting of fluorine, chlorine, ($C_1$-$C_4$)-alkoxy and ($C_3$-$C_7$)-cycloalkyl,
($C_3$-$C_7$)-cycloalkyl, where the cycloalkyl radical is unsubstituted or substituted by one or more substituents selected from the group consisting of fluorine, chlorine, ($C_1$-$C_4$)-alkyl and ($C_3$-$C_7$)-cycloalkyl and ($C_1$-$C_4$)-alkoxy, ($C_1$-$C_6$)-alkoxy, where the alkoxy radical is unsubstituted or substituted by one or more substituents selected from the group consisting of fluorine, chlorine, ($C_1$-$C_4$)-alkoxy and ($C_3$-$C_7$)-cycloalkyl, ($C_3$-$C_7$)-cycloalkoxy, where the cycloalkoxy radical is unsubstituted or substituted by one or more substituents selected from the group consisting of fluorine, chlorine, ($C_1$-$C_4$)-alkyl and ($C_1$-$C_4$)-alkoxy, CO—X, where X is $OR^{1''}$, $SR^{1''}$ or $NR^{2'}R^{2''}$, in which $R^{1''}$ is as defined for $R^1$ and $R^{1''}$ is the same as or different from $R^1$, and in which $R^{2'}$ and $R^{2''}$ are each independently H, ($C_1$-$C_6$) alkyl, substituted ($C_1$-$C_6$) alkyl, aryl or substituted aryl, or $R^{2'}$ and $R^{2''}$ form a ring, phenyl or 1-naphthyl or 2-naphthyl or a five- or six-membered heteroaromatic ring having 1 to 2 heteroatoms, where the heteroatoms are each independently selected from the group consisting of O and N, and where the aryl or heteroaryl radical is unsubstituted or substituted by one or more substituents selected from the group consisting of fluorine, chlorine, bromine, iodine, ($C_1$-$C_4$)-alkyl, ($C_1$-$C_4$)-alkoxy and ($C_3$-$C_7$)-cycloalkyl and ($C_1$-$C_4$)-alkylthio, and $R^5$ is H, ($C_1$-$C_6$) alkyl, substituted ($C_1$-$C_6$) alkyl, aryl or substituted aryl, Where this description refers to an "aniline", this means one of the abovementioned compounds of the formula (Q). A prerequisite for performance of the process is that the aniline used has a hydrogen atom in the ortho position to the amino group, meaning that the aniline used has to be unsubstituted in the ortho position. In addition, the aromatic ring of the aniline, aside from the amino group, may have up to four further substituents $R^{4a}$ to $R^{4d}$. Particular preference is given to disubstitution of the aniline (Q), meaning that two of the $R^{4a}$ to $R^{4d}$ radicals are not H.

Particular preference is given to anilines of the formula (Q) in which the $R^{4a}$ to $R^{4d}$ radicals are each independently H, F, Cl, Br, I, $CF_3$, CN, $NO_2$ or CO—X, where X is $OR^{1''}$, $SR^{1''}$ or $NR^{2'}R^{2''}$, in which $R^{1''}$ is defined for $R^1$ and $R^{1''}$ is the same as or different from $R^1$, and in which $R^{2'}$ and $R^{2''}$ are as defined for $R^2$, where $R^{2'}$ and $R^{2''}$ are each the same as or different from $R^2$, or $R^{2'}$ and $R^{2''}$ form a ring.

Very particular preference is given to only monosubstitution of the aniline, meaning that one of the $R^{4a}$ to $R^{4d}$ radicals is not H, such that the aniline reactants have one further substituent in addition to the amino group on the aromatic ring of the aniline.

A particularly preferred $R^{4a}$ to $R^{4d}$ radical is fluorine. It is very particularly preferred when $R^{4a}$, i.e. the radical in the ortho position to the amino group, is a fluorine, the rest of the aromatic ring of the aniline being unsubstituted.

Where this description refers to a "thioether", this means one of the abovementioned compounds of the formula (W). The thioether (W) used in the process according to the invention has the following structure:

(W)

in which
$R^1$ is ($C_1$-$C_6$) alkyl, substituted ($C_1$-$C_6$) alkyl, aryl or substituted aryl,
$R^2$ is an electron-withdrawing or activating substituent selected from the group consisting of CN,
$NO_2$,
CO—$R^{1'}$, where $R^{1'}$ is as defined for $R^1$ and $R^{1'}$ is the same as or different from $R^1$,
CO—X, where X is $OR^{1'''}$, $SR^{1'''}$ or $NR^{2'}R^{2''}$, in which $R^{1'''}$ is as defined for $R^1$ and $R^{1'''}$ is the same as or different from $R^1$, and in which
$R^{2'}$ and $R^{2''}$ are each independently H, ($C_1$-$C_6$) alkyl, substituted ($C_1$-$C_6$) alkyl, aryl or substituted aryl, or $R^{2'}$ and $R^{2''}$ alternatively form a ring,
SO(n)-$R^{1'''}$, where $R^{1'''}$ as defined for $R^1$, where each $R^{1'''}$ the same as or different from $R^1$ and where n is 0, 1 or 2,
aryl, and
heteroaryl, and
$R^3$ is H, ($C_1$-$C_6$) alkyl, substituted ($C_1$-$C_6$) alkyl, aryl or substituted aryl.

The compounds of the formulae (Q) and (W) usable in accordance with the invention are preparable by the processes known to those skilled in the art.

In connection with the chemical terms used in this description, the definitions customary to the person skilled in the art apply, unless specifically defined otherwise.

The alkyl, alkoxy, haloalkyl, haloalkoxy, alkylamino and alkylthio radicals, and the corresponding unsaturated and/or substituted radicals, in the carbon skeleton may each be straight-chain or branched. Unless stated specifically, in the case of these radicals, preference is given to the lower carbon skeletons, for example having 1 to 6 carbon atoms, or in the case of unsaturated groups to those having 2 to 6 carbon atoms. Alkyl radicals, including in the composite definitions such as alkoxy, haloalkyl etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl.

Cycloalkyl is a carbocyclic saturated ring system having preferably 3 to 8 carbon atoms, e.g. cyclopropyl, cyclobutyl, cyclopentyl or cyclohexyl.

Halogen is fluorine, chlorine, bromine or iodine. Haloalkyl is alkyl partly or fully substituted by halogen, preferably by fluorine, chlorine and/or bromine, especially by fluorine and/or chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A substituted alkyl is a ($C_1$-$C_6$) alkyl which is substituted by one or more radicals selected from the group consisting of ($C_1$-$C_6$) alkyl, ($C_1$-$C_6$) alkoxy, aryl, heteroaryl and halogen.

A substituted aryl is a mono-, bi- or polycyclic aromatic system, for example phenyl, naphthyl, tetrahydronaphthyl, indenyl, indanyl, pentalenyl, fluorenyl and the like, preferably phenyl, which is substituted by one or more substituents selected from the group consisting of ($C_1$-$C_6$) alkyl, ($C_1$-$C_6$) alkoxy, aryl, heteroaryl and halogen.

A heterocyclic radical or ring (heterocyclyl) may be saturated, unsaturated or heteroaromatic; it preferably contains one or more, especially 1, 2 or 3, heteroatoms in the heterocyclic ring, preferably from the group of N, O and S; it is preferably an aliphatic heterocyclyl radical having 3 to 7 ring atoms or a heteroaromatic radical having 5 or 6 ring atoms. The heterocyclic radical may, for example, be a heteroatomatic radical or ring (heteroaryl), for example a mono-, bi- or polycyclic aromatic system in which at least 1 ring contains one or more heteroatoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl and imidazolyl, or it is a partially or fully hydrogenated radical such as oxiranyl, pyrrolidyl, piperidyl, piperazinyl, dioxolanyl, oxazolinyl, isoxazolinyl, oxazolidinyl, isoxazolidinyl, morpholinyl, tetrahydrofuryl. Possible substituents for a substituted heterocyclic radical include the substituents mentioned below, and additionally also oxo. The oxo group may also occur on the ring heteroatoms which may exist in various oxidation states, for example in the case of N and S.

Substituted radicals such as a substituted alkyl, aryl, phenyl, benzyl, heterocyclyl and heteroaryl radical are, for example, a substituted radical derived from the unsubstituted base structure, where the substituents are, for example, one or more, preferably 1, 2 or 3, radicals from the group of halogen, alkoxy, haloalkoxy, alkylthio, hydroxyl, amino, nitro, carboxy, cyano, azido, alkoxycarbonyl, alkylcarbonyl, formyl, carbamoyl, mono- and dialkylaminocarbonyl, sulphamoyl, mono- and dialkylaminosulphonyl, substituted amino, such as acylamino, mono- and dialkylamino, and alkylsulphinyl, haloalkylsulphinyl, alkylsulphonyl, haloalkylsulphonyl and, in the case of cyclic radicals, also alkyl and haloalkyl; the term "substituted radicals" such as substituted alkyl etc. includes, as substituents, in addition to the saturated hydrocarbonaceous radicals mentioned, corresponding unsaturated aliphatic and aromatic radicals, such as optionally substituted phenyl, phenoxy etc. In the case of radicals having carbon atoms, preference is given to those having 1 to 4 carbon atoms, especially 1 or 2 carbon atoms. Preference is generally given to substituents from the group of halogen, e.g. fluorine or chlorine, ($C_1$-$C_4$) alkyl, preferably methyl or ethyl, ($C_1$-$C_4$) haloalkyl, preferably trifluoromethyl, ($C_1$-$C_4$) alkoxy, preferably methoxy or ethoxy, ($C_1$-$C_4$) haloalkoxy, nitro and cyano. Particular preference is given to the substituents methyl and fluorine.

The formulae (4), if applicable, also encompasses all stereoisomers. Such compounds contain one or more asymmetric carbon atoms which are unspecified in the general formulae. The possible stereoisomers defined by the specific three-dimensional shape thereof, such as enantiomers, diastereomers, can be obtained from mixtures of the stereoisomers by customary methods, or else prepared by stereoselective reactions in combinations with the use of stereochemically pure starting materials.

The anilines of the formula (Q) and thioethers of the formula (W) for use in accordance with the invention can be prepared by the processes known to those skilled in the art.

A further aspect of the invention relates to a multistage process for preparing compounds of the formula (1-1), or compounds of the formula (4-1), each of which have herbicidal action, proceeding from compounds of the formula (4), or compounds of the formula (4').

In the multistage process, the compounds of the formula (4) are first converted in the presence of an acid catalyst to an oxindole of the formula (7-1). Subsequently, the oxindoles of the formula (7-1) are converted in the steps according to scheme 5 to compounds of the formula (1-1) and N-alkyl-N-[2-(1,3,5-triazin-2-ylcarbonyl)phenyl]-alkanesulphonamides of the formula (4-1).

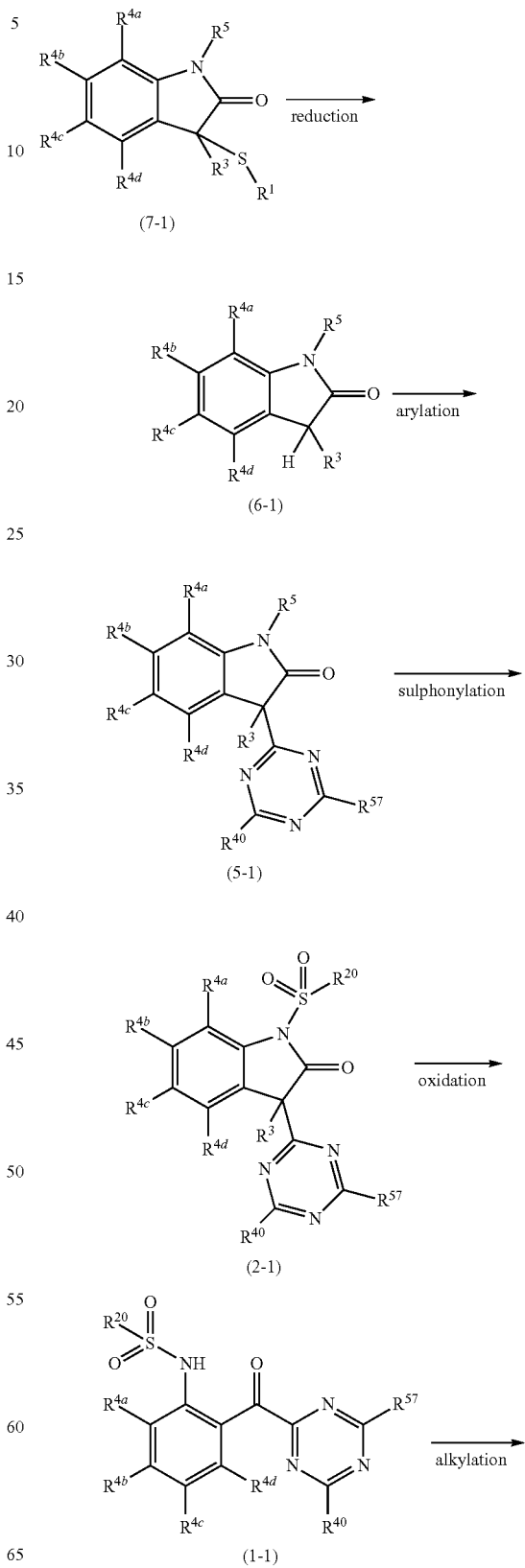

Scheme 5: Multistage process for preparing compounds of the general formulae (1-1) and (4-1) suitable for plant protection -continued

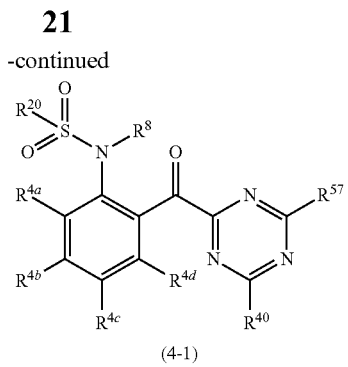

(4-1)

It is a feature of the multistage process, with respect to the previously known processes for preparing N-alkyl-N-[2-(1,3,5-triazin-2-ylcarbonyl)phenyl]-alkanesulphonamides (4-1) and 2-(triazinylcarbonyl)sulphonanilides (1-1), that the reactants or intermediates used are the ortho-substituted anilines of the formula (4), or oxindole compounds of the formula (7-1), obtained by means of a continuous reaction regime in a flow reactor. One aspect of the invention thus also encompasses the use of the ortho-substituted anilines of the formula (4) obtained in a flow reactor for preparation of N-alkyl-N-[2-(1,3,5-triazin-2-ylcarbonyl)phenyl]alkanesulphonamides of the formula (4-1).

The use of a flow reactor has the advantage that the process for preparing compounds of the formula (4-1) can be performed even more efficiently in the industrial scale compared to the previously known processes, and high yields can simultaneously be obtained.

The performance of the multistage process (overall process) is elucidated hereinafter: first of all, a compound of the formula (4) obtained in a continuous process using a flow reactor according to claim 1 is converted in the presence of an acid catalyst to a 3-(alkylsulphanyl)-1,3-dihydro-2H-indol-2-one of the formula (7-1). The preparation of oxindoles of the formula (7-1) proceeding from compounds of the formula (4), or here by way of example of the formula (4'), in which $R^2$ is preferably $CO_2R$ in which R in turn is more preferably methyl or ethyl (see scheme below), is characterized in that the compounds of the formula (4) prepared according to claim 1, after extraction of the tertiary amine, are admixed with an alcoholic HCl solution either directly in the reaction solution, or after the concentration of the reaction solution, and the mixture is stirred at a temperature between 0 to 40° C.

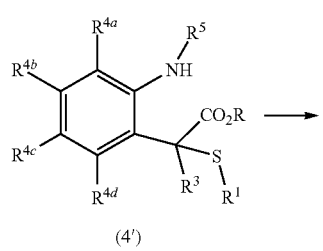

(4')

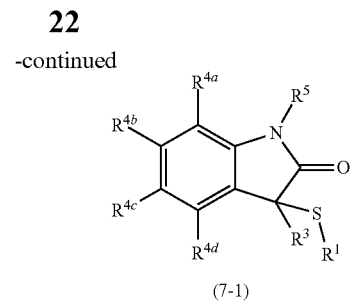

(7-1)

Alternatively, oxindoles of the formula (7-1) are prepared proceeding from compounds of the formula (4) in which $R^2$ is CO—X where X is SR''' or $NR^{2'}R^{2''}$, in which $R^{1'''}$ is as defined for $R^1$ and $R^{1'''}$ is the same as or different from $R^1$, and in which $R^{2'}$ and $R^{2''}$ are each independently H, $(C_1-C_6)$ alkyl, substituted $(C_1-C_6)$ alkyl, aryl or substituted aryl, or $R^{2'}$ and $R^{2''}$ form a ring.

Subsequently, the 3-(alkylsulphanyl)-1,3-dihydro-2H-indol-2-one of the formula (7-1), obtained by the aforementioned procedure from a compound of the formula (4) or (4'),

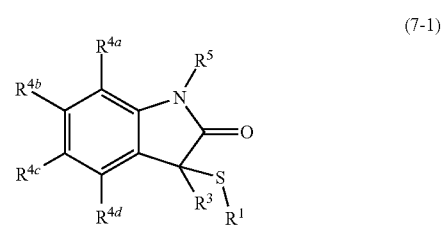

(7-1)

in which
$R^1$ is an unsubstituted $(C_1-C_6)$ alkyl, a substituted $(C_1-C_6)$ alkyl, an unsubstituted aryl or a substituted aryl,
$R^3$ is hydrogen,
$R^{4a}$ to $R^{4d}$ are each as defined for formula (4),
$R^5$ is hydrogen,
is converted by
reduction to a 1,3-dihydro-2H-indol-2-one (6-1)

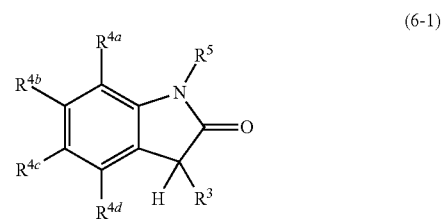

(6-1)

in which
$R^{4a}$ to $R^{4d}$, $R^3$ and $R^7$ are each as defined for formula (7-1).

Preference is given to the reaction of compounds of the formula (7-1) in which $R^5$ is an unsubstituted or substituted $(C_1-C_4)$-alkyl, a $(C_3-C_7)$-cycloalkyl, a benzyl or a $CH_2$—C(O)O—$(C_1-C_6)$-alkyl.

The compounds of the formula (6-1) obtained by means of reduction are converted to a herbicide of the formula (4-1) by the reaction steps summarized in scheme 5, i.e. the steps of arylation, sulphonylation, oxidation and alkylation.

For preparation of N-alkyl-N-[2-(1,3,5-triazin-2-ylcarbonyl)phenyl]alkanesulphonamides of the formula (4-1)

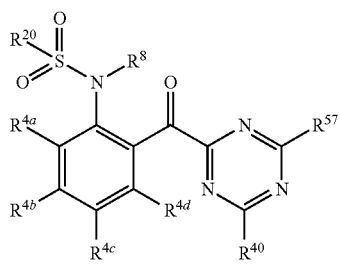

(4-1)

in which
$R^{4a}$ to $R^{4d}$ are each as defined for compounds of the formula (4), or of the formula (Q), and
$R^8$ is
  ($C_1$-$C_6$)-alkyl, where the alkyl radical is unsubstituted or fully or partly substituted by fluorine,
  ($C_1$-$C_6$)-cycloalkyl, ($C_1$-$C_6$)-alkenyl or ($C_1$-$C_6$)-alkoxyalkyl, where each of these radicals is unsubstituted or fully or partly substituted by fluorine, and
$R^{20}$ is
  ($C_1$-$C_6$)-alkyl, where the alkyl radical is unsubstituted or fully or partly substituted by fluorine, or
  ($C_3$-$C_7$)-cycloalkyl, where the cycloalkyl radical is unsubstituted or fully or partly substituted by fluorine, and
$R^{40}$ and $R^{57}$ are each independently
  hydrogen,
  ($C_1$-$C_6$)-alkyl, where the alkyl radical is unsubstituted or substituted by one or more substituents selected from the group consisting of fluorine, chlorine, ($C_1$-$C_4$)-alkoxy or ($C_3$-$C_7$)-cycloalkyl,
  ($C_1$-$C_6$)-alkoxy, where the alkoxy radical is branched or unbranched and is unsubstituted or substituted by one or more substituents selected from the group consisting of fluorine, chlorine, ($C_1$-$C_4$)-alkoxy or ($C_3$-$C_7$)-cycloalkyl,
proceeding from a 1,3-dihydro-2H-indol-2-one of the formula (6-1)

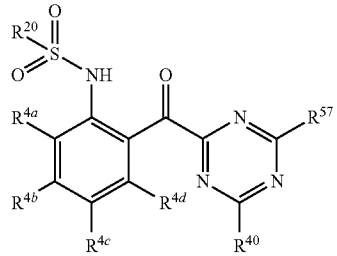

(6-1)

in which
$R^{4a}$ to $R^{4d}$ are each as defined for formula (4),
$R^3$ is hydrogen, and
$R^5$ is hydrogen, in a
first step by
arylation to give a triazinyl-substituted oxindole of the formula (5-1)

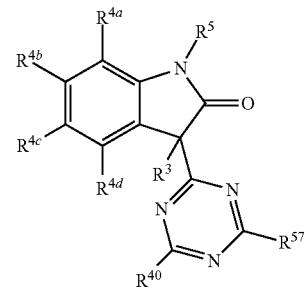

(5-1)

in which
$R^{4a}$ to $R^{4d}$ and $R^{40}$ and $R^{57}$ are each as defined for the formula (4-1) and $R^3$ and
$R^7$ are each as defined for the formula (6-1),
and the arylation products of the formula (5-1) are converted in a
second step by
sulphonylation to give N-sulphonyl-substituted 3-triazinyloxindoles of the formula (2-1)

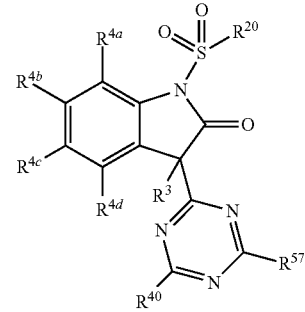

(2-1)

in which
$R^{4a}$ to $R^{4d}$, $R^{20}$, and $R^{40}$ and $R^{57}$ are each as defined in formula (4-1) and $R^3$ is as defined for the formula (6-1),
and the sulphonylation products of the formula (2-1) are converted in a
third step by
oxidative ring opening to give a 2-(triazinylcarbonyl)sulphonanilide of the formula (1-1)

(1-1)

in which
$R^{4a}$ to $R^{4d}$, $R^{20}$, and $R^{40}$ and $R^{57}$ are each as defined for formula (4-1),
and the oxidation products of the formula (1-1) are converted in a fourth step by
alkylation to give an N-alkyl-N-[2-(1,3,5-triazin-2-ylcarbonyl)phenyl]-alkanesulphonamide of the formula (4-1)

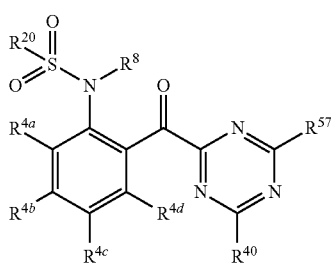

(4-1)

in which
$R^{4a}$ to $R^{4d}$, $R^{20}$ and $R^{40}$ and $R^{57}$ are each as defined for formula (4-1),
wherein
the alkylating reagent used is
X—$R^8$, in which X is chlorine, bromine, iodine or $OSO_2R^9$, where $R^8$ is as defined above for formula (4-1) and $R^9$ is as defined above for $R^1$, or
$(R^8)_2SO_4$, in which $R^8$ is as defined above for formula (4-1).

Thus, the multistage process for preparing N-alkyl-N-[2-(1,3,5-triazin-2-ylcarbonyl)-phenyl]alkanesulphonamides of the formula (4-1), as well as the process for preparing oxindoles of the formula (7-1) performed in a flow reactor according to claim 1 of the present invention, comprises five further component steps, each of which were the subject of prior applications. These component steps and the execution thereof are elucidated briefly hereinafter:

reduction of substituted or unsubstituted 3-(alkylsulphanyl)-1,3-dihydro-2H-indol-2-ones (7-1) to substituted or unsubstituted 1,3-dihydro-2H-indol-2-ones (6-1). This process is possible on the industrial scale and is described in the patent application with application number EP 10162381.7. With regard to the executability of the reduction, reference is made here to the content of the patent application with the application number EP 10162381.7.

The reduction is characterized in that
a) a compound of the formula (7-1) is dissolved or suspended in a polar solvent,
b) a sulphur-containing salt is added to the solution or suspension, and
c) the reaction mixture is heated under reflux at a temperature corresponding to not more than the boiling temperature of the polar solvent.

Particularly preferred sulphur-containing salts for performance of the reduction are sodium salts selected from the group consisting of sodium bisulphite, sodium sulphite, sodium thionite, sodium dithionite and sodium thiosulphate.

Arylation of substituted or unsubstituted 1,3-dihydro-2H-indol-2-ones (6-1) to triazinyl-substituted oxindoles (5-1). This process is possible on the industrial scale and is described in the patent application with the application number EP 10196205.8. With regard to the executability of the arylation, reference is made here to the content of the patent application with application number EP 10196205.8.

The arylation is characterized in that it is performed in the presence of
a carbonate, or
a hydroxide, or
a phosphate, or
in a mixture comprising at least two of the aforementioned bases.

Preferably, the bases used in the arylation are potassium carbonate, sodium carbonate, sodium hydroxide, potassium hydroxide or an at least two-component mixture consisting of at least one of the two carbonates: potassium carbonate and sodium carbonate, and of at least one of the two hydroxides: potassium hydroxide or sodium hydroxide.

Sulphonylation of triazinyl-substituted oxindoles (5-1) to give N-sulphonyl-substituted 3-triazinyloxindoles (2-1). This process is possible on the industrial scale and is described in the patent application with application number EP 11159875.1. With regard to the executability of the sulphonylation, reference is made here to the content of the patent application with the application number EP 11159875.1.

The sulphonylation is characterized in that it is effected in the presence of
a 1-substituted imidazole base, or
a base mixture containing at least one 1-substituted imidazole base.

Particularly preferred imidazole bases for the performance of the sulphonylation are 1-methyl-1H-imidazole, 1-butyl-1H-imidazole or 1-benzyl-1H-imidazole, which can be used individually or in a mixture, very particular preference being given to the use of 1-methyl-1H-imidazole.

Oxidative ring opening of N-sulphonyl-substituted 3-triazinyloxindoles (2-1) to give 2-(triazinylcarbonyl)sulphonanilides (1-1). This process is possible on the industrial scale and is the subject of the patent application with reference number PCT/EP2011/073287.

Alkylation of 2-(triazinylcarbonyl)sulphonanilides (1-1) to give N-alkyl-N-[2-(1,3,5-triazin-2-ylcarbonyl)phenyl]alkanesulphonamides (4-1). This process is described in patent application WO 2006/008159 A1. With regard to the executability of the alkylation, reference is made here to the content of patent application WO 2006/008159 A1.

The alkylation can be effected with standard alkylating agents. In the case of a methylation, preference is given to using dimethyl sulphate.

The herbicidal action (see WO 2007/031208 A2) and fungicidal action (see WO 2006/008159 A1) of N-alkyl-N-[2-(1,3,5-triazin-2-ylcarbonyl)phenyl]alkanesulphonamides of the formula (4-1) has long been known.

Thus, the aforementioned details of the executability of the multistage overall process, comprising the preparation of the compounds of the formula (4) in a flow reactor, the conversion of the compounds of the formula (4) to oxindoles of the formula (7-1) and the subsequent arylation, sulphonylation, oxidation and alkylation thereof, demonstrate the suitability of compounds of the formula (4) and the suitability of oxindoles of the formulae (7-1), (6-1), (5-1), (2-1) and of compounds of the formula (1-1), for preparation of crop protection agents of the formula (4-1).

EXAMPLES

The example which follows illustrates the process according to the invention in detail, without restriction thereof.

In the elucidations of the example, stated amounts are based on weight, unless specifically defined otherwise (in the description, % by weight=percent by weight was used analogously for this purpose). For units of measurement, physical parameters and the like, standard abbreviations are used, for example h=hour(s), mpt.=melting point, l=liter, ml=milliliter, g=gram, min=minute(s), in vacuo=under reduced pressure, of theory=percent yield according to theory.

Synthesis Example 1

Continuous Performance of a Gassman Reaction Using the Nitrogen Base Quinoline

Scheme 6 below shows the structure of a flow reactor suitable for the execution of the process according to the invention.

Reservoir 1 (RC1) of the flow reactor is charged with a solution of 7.5 parts by mass of 2-fluoroaniline (2-FA), 1.66 parts by mass of quinoline (QL) and 90.84 parts by mass of dichloromethane (DCM). A solution of 7.5 parts by mass of sulphuryl chloride ($SO_2Cl_2$; in scheme 6: SO2Cl2) and 92.5 parts by mass of dichloromethane is introduced into reservoir 2 (RC2) of the flow reactor. A solution of 7.96 parts by mass of methyl methylthioacetate (MMTA), 4.88 parts by mass of quinoline and 87.16 parts by mass of dichloromethane is introduced into reservoir 3 (RC3) of the flow reactor. Pure quinoline is introduced into reservoir 4 (RC4) of the flow reactor.

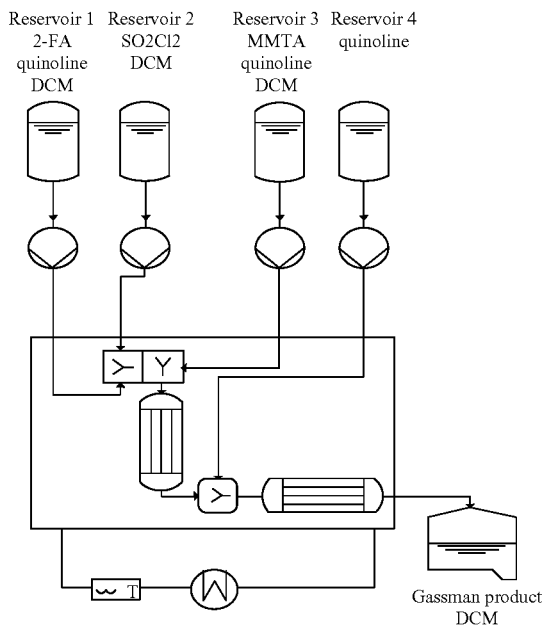

Scheme 6-Structure of flow reactor

Reservoir 1  Reservoir 2  Reservoir 3  Reservoir 4
2-FA         SO2Cl2       MMTA         quinoline
quinoline    DCM          quinoline
DCM                       DCM Gassman product
DCM The individual components of the flow reactor and the reactants and solvents used in the continuous reaction are referred to by the abbreviations elucidated hereinafter:
RC reservoir/reservoir chamber
RM reservoir mixture
M mixing chamber
DE dwell element
CV collecting vessel 2-FA 2-fluoroaniline
QL quinoline
DCM dichloromethane
MMTA methyl methylthioacetate
SO2Cl2 sulphonyl chloride ($SO_2Cl_2$)

From the reservoirs 1 and 2, the substrate solutions made up are cooled by means of supply temperature control zones to the reaction temperature (−40° C.) and reacted in a first static mixing chamber (M1) having a volume of 0.3 cm³. The conveying performance of the pumps is selected so as to achieve a dwell time of 0.16 second and such that a stoichiometric ratio of 2-fluoroaniline to sulphuryl chloride of 1.05 is present. The reaction mixture leaves the first static mixing chamber (M1) and flows directly into a second static mixing chamber (M2) with volume 0.6 cm³.

In the second static mixing chamber (M2), the reaction solution is reacted with the substrate stream brought to reaction temperature, consisting of methyl methyl thioacetate, quinoline and dichloromethane, from reservoir 3. The conveying performance of the pump is selected so as to achieve a dwell time of 0.22 second and such that a stoichiometric ratio of methyl methylthioacetate to sulphuryl chloride of 1.05 is present.

The reaction mixture leaves the second mixing chamber and flows into a first dwell element (DE1) with volume 90.84 cm³ and a dwell time of 32.6 seconds. Connected to the dwell element DE1 is a further third static mixing chamber (M3) with a volume of 0.3 cm³. In the third static mixing chamber (M3), the reaction solution is reacted with the quinoline stream from reservoir 4 (RC4) which has been brought to reaction temperature. The conveying performance of the pump was selected so as to achieve a dwell time of 0.15 second and such that a stoichiometric ratio of sulphuryl chloride to quinoline of 1.00 is present.

The reaction mixture leaves the third mixing chamber and flows into a second dwell element (DE2) with a volume of 5.7 cm³ and a dwell time of 2 seconds. The reaction mixture is subsequently collected in a collecting vessel (CV 1). The reaction is monitored regularly by HPLC.

The reaction mixture is passed into 0.4 N HCl at 0° C. The pale yellow organic phase is separated from the aqueous phase. The organic phase is extracted with 0.4 N HCl, such that the product 4 is present as a solution in dichloromethane.

Subsequently, methanolic HCl is added and the reaction mixture is stirred at RT for 5 hours. The reaction solution is concentrated down to 26 mbar at 40° C. The residue is diluted with butyl acetate and admixed with n-heptane. After stirring the reaction mixture at RT for 4 h, the crystallization is complete. The product is filtered off and washed twice with n-heptane. The conversion product of the formula (7-1) which results from the aforementioned final treatment was isolated with an overall yield of 78%.

The invention claimed is:

1. Process for continuously preparing a compound of formula (4)

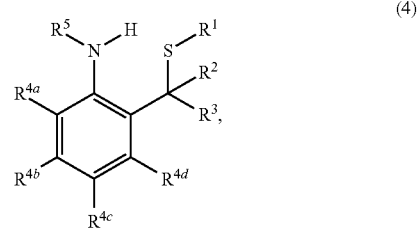

(4)

in which
R$^1$ is (C$_1$-C$_6$) alkyl, substituted alkyl, aryl or substituted aryl,
R$^2$ is an electron-withdrawing or activating substituent selected from the group consisting of
CN,
NO$_2$,
CO—R$^{1'}$, where R$^{1'}$ is as defined for R$^1$ and R$^{1'}$ is the same as or different from R$^1$,
CO—X, where X is OR$^{1''}$, SR$^{1''}$ or NR$^{2'}$R$^{2''}$, in which R$^{1''}$ is as defined for R$^1$ and R$^{1''}$ is the same as or different from R$^1$, and in which
R$^{2'}$ and R$^{2''}$ are each independently H, (C$_1$-C$_6$) alkyl, substituted (C$_1$-C$_6$) alkyl, aryl or substituted aryl, or R$^{2'}$ and R$^{2''}$ form a ring,
SO(n)-R$^{1'''}$ where R$^{1'''}$ is as defined for R$^1$, where each R$^{1'''}$ is the same as or different from R$^1$ and where n is 0, 1 or 2,
aryl, and
heteroaryl,
R$^3$ is H, (C$_1$-C$_6$) alkyl, substituted alkyl, aryl or substituted aryl,
R$^{4a}$ to R$^{4d}$ are each independently selected from the group consisting of hydrogen, fluorine, chlorine, bromine, iodine, CN, NO$_2$, and from
(C$_1$-C$_6$)-alkyl, where the alkyl radical is unsubstituted or substituted by one or more substituents selected from the group consisting of fluorine, chlorine, (C$_1$-C$_4$)-alkoxy and (C$_3$-C$_7$)-cycloalkyl,
(C$_3$-C$_7$)-cycloalkyl, where the cycloalkyl radical is unsubstituted or substituted by one or more substituents selected from the group consisting of fluorine, chlorine, (C$_1$-C$_4$)-alkyl and (C$_3$-C$_7$)-cycloalkyl and (C$_1$-C$_4$)-alkoxy,
(C$_1$-C$_6$)-alkoxy, where the alkoxy radical is unsubstituted or substituted by one or more substituents selected from the group consisting of fluorine, chlorine, (C$_1$-C$_4$)-alkoxy and (C$_3$-C$_7$)-cycloalkyl,
(C$_3$-C$_7$)-cycloalkoxy, where the cycloalkoxy radical is unsubstituted or substituted by one or more substituents selected from the group consisting of fluorine, chlorine, (C$_1$-C$_4$)-alkyl and (C$_1$-C$_4$)-alkoxy,
CO—X, where X is OR$^{1''}$, SR$^{1''}$ or NR$^{2'}$R$^{2''}$, in which R$^{1''}$ is as defined for R$^1$ and R$^{1''}$ is the same as or different from R$^1$, and in which R$^{2'}$ and R$^{2''}$ are each independently H, (C$_1$-C$_6$) alkyl, substituted (C$_1$-C$_6$) alkyl, aryl or substituted aryl, or R$^{2'}$ and R$^{2''}$ alternatively form a ring,
phenyl or 1-naphthyl or 2-naphthyl or a five- or six-membered heteroaromatic ring having 1 to 2 heteroatoms, where the heteroatoms are each independently selected from the group consisting of O and N, and where the aryl or heteroaryl radical is unsubstituted or substituted by one or more substituents selected from the group consisting of fluorine, chlorine, bromine, iodine, (C$_1$-C$_4$)-alkyl, (C$_1$-C$_4$)-alkoxy and (C$_3$-C$_7$)-cycloalkyl and (C$_1$-C$_4$)-alkylthio, and
R$^5$ is H, (C$_1$-C$_6$) alkyl, substituted (C$_1$-C$_6$) alkyl, aryl or substituted aryl,
in which reactants are used in a flow reactor in the presence of an organic solvent comprising
an aniline (Q)

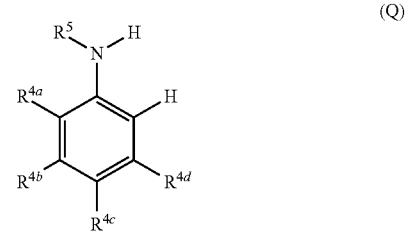

in which
R$^4$, n and R$^5$ are each as defined for compounds of formula (4), and
a thioether (W)

in which
R$^1$, R$^2$ and R$^3$ are each as defined for compounds of formula (4),
wherein reactants of formulae (Q) and (W) are converted in the presence of
a chlorinating agent, and
at least one nitrogen base having no NH group.

2. Process for preparing a compound of formula (4) in a flow reactor according to claim 1, wherein the reaction temperature is in a range between −65° C. and 0° C.

3. Process for preparing a compound of formula (4) in a flow reactor according to claim 2, wherein the reaction temperature is in a range between −55° C. and −10° C. or between −45° C. and −20° C.

4. Process for preparing a compound of formula (4) in a flow reactor according to claim 1, wherein the nitrogen base or nitrogen bases are selected from the group consisting of
tertiary amines N(R$^{60}$)$_3$ (P), in which the R$^{60}$ radicals are selected from the group of the substituted or unsubstituted C$_1$-C$_{18}$ alkyl and substituted or unsubstituted (C$_1$-C$_6$) aryl radicals,
cyclic tertiary amines,
substituted and unsubstituted pyridines, and
benzofused ring systems of substituted or unsubstituted pyridines.

5. Process for preparing a compound of formula (4) in a flow reactor according to claim 4, wherein at least one of the nitrogen bases is a tertiary amine N(R$^{60}$)$_3$ (P) in which the R$^{60}$ radicals are each a substituted or unsubstituted C$_1$-C$_{18}$ alkyl, where at least one of the R$^{60}$ radicals has a chain length of at least C$_6$-C$_{18}$ or the R$^6$ radicals together have a total chain length of at least C$_6$-C$_{18}$.

6. Process for preparing a compound of formula (4) in a flow reactor according to claim 1, wherein the nitrogen base is selected from the group consisting of
tributylamine,
2-methyl-5-ethylpyridine, and
unsubstituted quinoline.

7. Process for preparing a compound of formula (4) in a flow reactor according to claim 1, wherein a mixture comprising at least two of the nitrogen bases selected from the group consisting of tributylamine,
2-methyl-5-ethylpyridine and
unsubstituted quinoline
is used.

8. Process for preparing a compound of formula (4) in a flow reactor according to claim 1, wherein the solvents used are at least one selected from the group consisting of
chloroalkanes,
aromatics,
haloaromatics, and
substituted aromatics.

9. Process for preparing a compound of formula (4) in a flow reactor according to claim 1, wherein the chlorinating agent is selected from the group consisting of
tert-butyl hypochlorite,
sulphuryl chloride, and
a mixture of tert-butyl hypochlorite and sulphuryl chloride.

10. Process for preparing a compound of formula (4) in a flow reactor according to claim 1, wherein at least one of the two reactants of formula (Q) and of formula (W), before addition of the chlorinating agent,
is dissolved in an organic solvent, and
is mixed with at least one nitrogen base not having an NH group and present dissolved in the selected organic solvent at a respective reaction temperature.

11. Process for preparing a compound of formula (4) in a flow reactor according to claim 1, wherein the nitrogen base or a mixture comprising one or more nitrogen bases of which none have an NH group are supplied more than once, optionally repeatedly, to various reservoir chambers (RC) and/or mixing chambers (M) and/or dwell zones (DZ) which form part of a flow reactor.

12. Process for preparing a compound of formula (4) in a flow reactor according to claim 11, wherein a first reservoir chamber (RC1) of the flow reactor is initially charged with a reservoir mixture 1 (RM1) at least comprising
an aniline (Q):

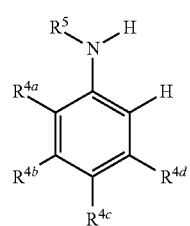

(Q)

in which the $R^4$ radicals, n and $R^5$ radicals are each as defined in formula (4),
an organic solvent in which the aniline (Q) is dissolved, and
at least one nitrogen base not having an NH group,
and
a second reservoir chamber (RC2) of the flow reactor is initially charged with a reservoir mixture 2 (RM2) at least comprising
a liquid chlorinating agent and
an organic solvent corresponding to the solvent present in the first reservoir chamber,
and
then reservoir mixture 1 (RM1) and reservoir mixture 2 (RM2) are mixed in a first mixing chamber (M1) at a reaction temperature in a range between −65° C. and 0° C. or between −45° C. and −20° C., and
then the reaction mixture from the first mixing chamber (M1) is combined in a second mixing chamber (M2) with a reservoir mixture 3 (RM3) initially charged in a third reservoir chamber (RC3) of a flow reactor, at least comprising
a thioether (W)

(W)

in which the $R^1$, $R^2$ and $R^3$ radicals are each as defined in formula (4),
an organic solvent corresponding to the solvent initially charged in the first reservoir chamber, and
a nitrogen base which does not have an NH group and corresponds to the nitrogen base initially charged in the first reservoir chamber,
and the mixture thus obtained
is then converted in a first dwell element 1 (DE-1) of the flow reactor, and
then the mixture converted in the dwell element 1 (DE-1) is mixed again in a third mixing chamber (M3) of the flow reactor with that nitrogen base which does not have an NH group and corresponds to the nitrogen base initially charged in the first reservoir chamber, and the mixture thus obtained
is then converted again in a second dwell element 2 (DE-2) of the flow reactor to give a compound of formula (4).

* * * * *